(12) United States Patent
Lockett

(10) Patent No.: US 9,226,844 B2
(45) Date of Patent: Jan. 5, 2016

(54) APPARATUS FOR SACRO-LUMBAR BACK SUPPORT, REDUCTION OF LOAD ON VERTEBRAE DISCS AND STIMULATION OF CIRCULATION AND MUSCLES THROUGH AXIAL TENSIONING EXERCISES

(71) Applicant: John Hoyl Lockett, Prairie Village, KS (US)

(72) Inventor: John Hoyl Lockett, Prairie Village, KS (US)

( * ) Notice: Subject to any disclaimer, the term of this patent is extended or adjusted under 35 U.S.C. 154(b) by 53 days.

(21) Appl. No.: 14/043,754

(22) Filed: Oct. 1, 2013

(65) Prior Publication Data

US 2015/0094632 A1    Apr. 2, 2015

(51) Int. Cl.
*A61F 5/00* (2006.01)
*A61F 5/02* (2006.01)

(52) U.S. Cl.
CPC .. *A61F 5/02* (2013.01); *A61F 5/028* (2013.01)

(58) Field of Classification Search
CPC ........ A61H 1/022; A61H 1/0229; A61F 5/02; A61F 5/027; A61F 5/024; A61F 5/026
USPC ............................ 602/19, 32, 35, 36; 128/876
See application file for complete search history.

(56) References Cited

U.S. PATENT DOCUMENTS

| 4,750,479 | A  | * | 6/1988 | Schawl | 602/32 |
|---|---|---|---|---|---|
| 5,258,017 | A | * | 11/1993 | Myers et al. | 606/241 |
| 5,375,279 | A | * | 12/1994 | Toso | 5/657 |
| 5,722,940 | A | * | 3/1998 | Gaylord et al. | 602/19 |
| 2003/0195092 | A1 | * | 10/2003 | Basting | 482/124 |
| 2009/0093745 | A1 | * | 4/2009 | Chitwood et al. | 602/32 |
| 2012/0123310 | A1 | * | 5/2012 | Gazayerli | 602/36 |
| 2014/0200499 | A1 | * | 7/2014 | Champion | 602/36 |

* cited by examiner

*Primary Examiner* — Kristen Matter

(57) ABSTRACT

The invention is directed to the combination of orthopedic back support and physical exercise devices that provide comfort, support and stabilization of the spinal system. More particularly, it contributes to means for developing the musculature of the lower back, spinal cord and upper body by application of axial tensioning to unload compressive forces on the spine, thus allowing improved circulation to the discs and stimulation of the muscles. As a preventive exercise it helps avoid back problems, but when pain occurs, the invention helps relieve pain, improve comfort and provides rehabilitation of the back to a healthier state under self administration.

6 Claims, 14 Drawing Sheets

APPARATUS FOR SACRO-LUMBAR BACK SUPPORT, REDUCTION OF LOAD ON VERTEBRAE DISCS AND STIMULATION OF CIRCULATION AND MUSCLES THROUGH AXIAL TENSIONING EXERCISES

BACKGROUND OF INVENTION

1. Field of the Invention

The invention is directed to the combination of orthopedic back support and physical exercise devices that provide comfort, support and stabilization of the spinal system. More particularly, it contributes to means for developing the musculature of the lower back, spinal cord and upper body by application of axial tensioning to unload compressive forces on the spine, thus allowing improved circulation to the discs and stimulation of the muscles. As a preventive exercise it helps avoid back problems, but when pain occurs, the invention helps relieve pain, improve comfort and provides rehabilitation of the back to a healthier state under self administration.

Health statistics reveal that lower back pain is a very common and costly occurrence associated with a traumatic event, chronic occurrence, congenital or normal ageing process. Statistics reveal that there is an 80 percent probability that a person will have back problems during one's lifetime. In addition, back treatment is a $50 billion industry with a probable growth of 30 percent over the next twenty years. Despite the pervasiveness of the problem, at this time, a satisfactory solution is problematic due to the difficulty of analysis and uncertainty of results from various approaches for treatment. These treatments comprise home remedies, over-the-counter and prescription pain management, exercises, or stabilization of the lower back through the use of an orthotic back brace, or specialized orthotics, apparatus, or work methods to alter the way one works, walks, sits, or exercises in pursuit of pain relief and rehabilitation of the back. Surgical options are invasive and are reserved for the worst back injuries with results often far less than expectations.

2. Description of Related Art

Most devices in the field for lower back support rely on a circumferential belt used to contain a reservoir of body mass to constrain the movement of the spine. Such approaches have minimal effect in reducing the forces and compressive stresses on the discs between the vertebrae.

Prior art reflects various approaches for back support devises that consist principally of belt strapping systems that support pads, splines and methods of applying pressure to lumbar sections of the spinal musculature. In addition, they provide various means of girth adjustment, belt connections, or special functions. None reflect a trapeze approach for transferring forces to the pelvic musculature.

Partial relief can be obtained by an inversion table, but warnings for such treatment provide notice of the possibility of strokes.

More extensive relief can be obtained by professional traction tables, however, these subject the patient to compression of the lungs.

U.S. Pat. No. 5,551,085 to Leighton, ("Leighton"), and U.S. Pat. No. 7,364,558 B to Weaver, II et. al., ("Weaver"), reflect that improvements are still needed that balance both the support provided by the back brace with the comfort of wearing the brace. Neither provides the reduction of forces and stresses on the vertebra cells and cartilage nor the rehabilitative effect of physical exercise by axial tensioning of the spinal column.

Leighton discloses a lower back support with an elastic belt with lumbar pads pressured again the back when the overlapping pressure strap is tightened around the waist.

Weaver discloses a similar approach to improve a firmer support with improved comfort.

U.S. Design Pat. No. 435611 to Hines reveals adaptation of a belt strap for use in aerobic exercises.

U.S. Pat. No. 5,533,961 to Iwata features adaptation of vertical support bones for firmer support and stability.

DJO Global supplies Chattanooga traction tables that provide decompression of the back under professional treatment by separating tables that hold a patient in place by strapping belts.

An advertisement in Skymall magazine features a floor bench which by use of underarm supports and a lever that slides a tubular extension holding the feet stretches the back. Similar models are produced by Stamina Products.

The above references reflect the wide range of approaches that seek to provide relief of pain, comfort, stability and exercise for the back. None of these combine features that are integral in the current invention.

Most importantly, these noted inventions provide no personal, portable, and reasonably priced means or methods for axial tensioning of the spine to unload compressive forces. In addition to comfort and support features, the device of this patent application stimulates circulation and restores health to the back through exercise routines made possible by the apparatus.

BRIEF SUMMARY OF THE INVENTION

The present invention reasonably achieves the claims of the above related art with improvements that achieve the distinct advantage of axial tensioning treatment and exercises for rehabilitating the vertebrae and musculature of the spinal system and upper body.

The invention provides multi-purpose effects and is defined by four principal levels of embodiment; (1) Basic, (2) Standard, (3) Premium and (4) Custom. Alternatives to parts of these principal embodiments provide a broader range of treatments and exercises.

PRINCIPAL EMBODIMENTS

Basic

The Basic embodiment incorporates a non-elastic belt placed around the waist with the top just above the point of the iliac crest as it passes around the hip. Due to the conical shape of the hip, the belt slopes downward to a Velcro fastener—the right end segment of ties and the left end segment of loops—which are sewn to the belt at a slight angle so the fastener is horizontal when approximately centered in the front below the navel.

Attached to the belt on each side of the wearer, a trapeze assembly is centered on the iliac crest in such position that a vertical force can be applied downward on the trapeze bar until the belt prevents further displacement.

The trapeze assembly consists of a header support, "gusset," that is fastened to the belt, support ropes, "web straps," attached to the header, and the trapeze bar, "handle," connected at each end to the ropes.

In the Basic embodiment, the web straps, in this case serving as the gusset, are sewn to the belt and extended downward to be terminated by a loop in the strap to support the handle. The handle is reduced in diameter near each end to accept the web straps and hold them in place. Height adjustment of the handles is accomplished by adding adjustment loops to the web straps.

Principal Embodiments

Standard

The Standard embodiment incorporates the addition of a wider inner elastic belt connected in the middle of the back of the basic belt which remains as the outer belt. The inner belt is connected in front by an upgrade of the basic Velcro connection consisting of a right front end segment of loops and a left front end segment of ties.

The inner belt is wider to provide more comfort and stability and alternatively may include compressible pads with a fabric cover sewn to the interior side of the inner belt.

In the Standard embodiment, the basic belt, now the outer belt, is modified to better distribute the forces from the trapeze assembly to vertical resultant forces at the iliac crest. The existing belt portion is lowered to the top of the iliac crest so an additional top belt segment can be formed at each side around the conical surface above the iliac crest at the waist. This top belt would have a greater slope toward the front and back since there is a lower angle of conical slope. This top belt segment reduces the waist dimension and better distributes the path of forces from the trapeze assembly downward through the belt to the vertical resultant forces in the hips and legs.

The end sections of the top belt and basic existing belt are joined at the front in the Velcro connection and at the back by a gusset. The Velcro portions are shaped like the palm of a hand to provide better connections at various slopes of the end segments of the belt.

The embodiment of the Standard Belt also includes improvements in the trapeze assembly to provide improved vertical adjustment of the handle height.

Trapeze Embodiment A

Belt

A strap keeper loop hangs from a gusset attached to the outer belt. A belt lead with punched holes which will engage the belt buckle hangs from the strap keeper loop. The belt buckle strap threads through the buckle loop and is sewn together and likewise the other end wraps around the handle and is sewn together.

Trapeze Embodiment B

Conway

A strap keeper loop is attached to the belt by a tab gusset and another strap keeper loop is attached by looping the strap around the handle and sewing the loose end to the strap. A Conway buckle is used for adjustment of a third strap which contains spaced holes in it and passes up through the buckle, around the top strap keeper loop, back thru the buckle, around the bottom strap keeper loop, and back up through the buckle. With spaced holes the strap can be adjusted to various lengths to adjust the height of the handles.

Trapeze Embodiment C

Snap Latch and Slide

A strap keeper loop is attached to the belt by a tab gusset and another strap keeper loop is attached by looping the strap around the handle and sewing the loose end to the strap. A male portion of a snap latch is attached to a top strap that is supported by the top strap keeper loop. The female portion is attached to a strap with an adjustable slide keeper which in turn is attached to the strap keeper loop attached to the handle thus providing vertical adjustment.

Principal Embodiments of Premier and Custom Designs

Custom designs are included and defined in the "Detailed Description of the Product."

Principal Embodiment

Premier

The embodiments of the premier device provide improved comfort, fit, flexibility and durability in the use of the present invention. Plastic formed side elements with gel comfort pads provide improved bearing contact for the application of trapeze forces to the musculature of the pelvis. In addition, the elements provide connections for the basic, standard and premier belt devices to allow adjustments in the back, frontal and trapeze hangar segments. The inner belt provides various ways to add back support splines, lumbar supports and pads for stability and comfort.

Principal Embodiment

Custom

The embodiments of the custom device anticipate the special fabrication needs to meet the requirements of the wearer with physical limitations. The overhead option for applying downward forces to the trapeze segment provides a horizontal overhead bar so the wearer can perform a pull up exercise by grabbing the bar or attached handles or rings. The forces from the horizontal bar would then be transferred to structural frames on each side of the body that would further transfer the forces downward to the trapeze segment. The resulting force on the trapeze would be similar to the basic, standard and premier devices and axial tensioning of the spine would occur in the same manner. The side frames would have vertical adjustments to accommodate varying arm lengths, and special attachments to the frames and belt would be available for strapping the wearer as needed to accommodate physical limitations.

This invention simply provides an inner elastic belt with liner for comfortable adjustment of the apparatus around the waist of the wearer, an outer non-elastic belt that provides a peripheral band supported by the iliac crest from which handle assemblies at each side provide for axial tensioning of the spine by extension of force through the arms to the handle, thus elongating and tensioning the spine. The effect of axial tensioning is to unload the compressive forces on the spine and relieve pain, stimulate and increase the flow of blood to the spinal discs which are under reduced pressure, and invigorate the muscular development of the spinal muscles due to the effect of repeated exercises.

REFERENCE NUMERALS

Basic

Figure 1:
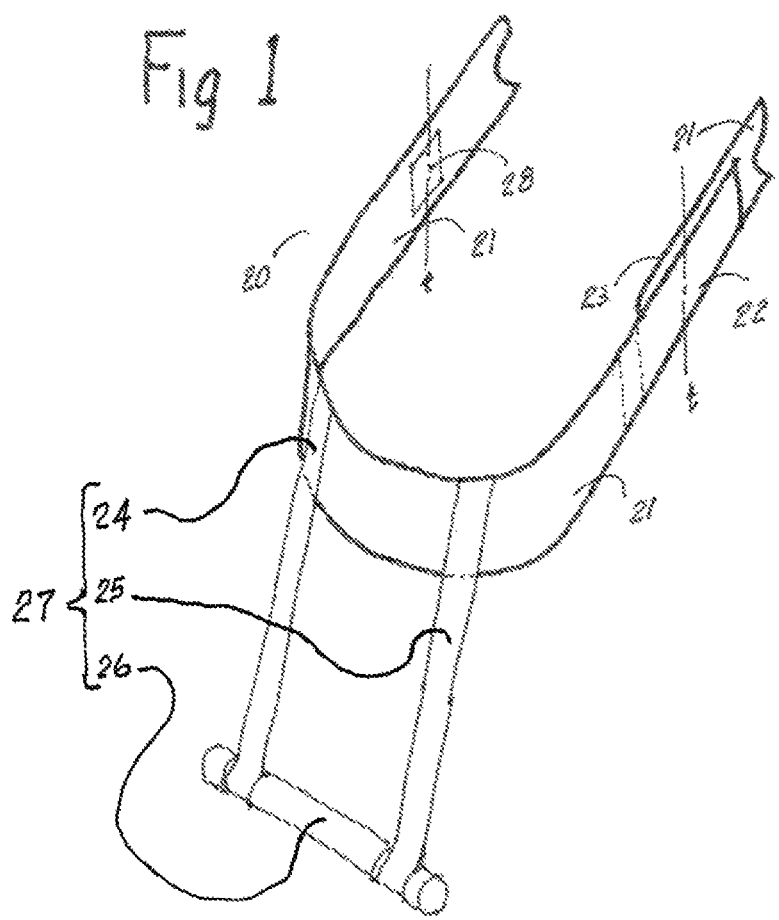
FIG. 1. Isometric View of the Basic Belt

1.-19. Not Used
21. Non-Elastic Belt Webbing
22. Velcro Connection Belt Loop End
23. Velcro Connection Belt Tie End
24. Trapeze Hangar Web Strap Gusset
25. Trapeze Hangar Web Strap with Loop
26. Trapeze Bar Handle
27. Reference to Trapeze Details [24, 25, 26]—Basic
28. Optional Velcro Back Tie Connection
29. Not Used

Standard

30. Standard Belt
31. Top Belt Addition
32.-33. Not Used
34. Velcro Palm Connection Loop End
35. Velcro Palm Connection Tie End
36. Reference to Trapeze Detail Options—Standard
37.-39. Not Used

Premium

40. Premium Belt
41. Lower Belt Addition
42. Back Gusset Addition
43. Side Gusset Additions
44. Front Gusset Additions
45. Back Velcro Tie Connection
46. Reference to Trapeze Details
47. Front Velcro Loop Connection
48. Front Velcro Tie Connection
49. Not Used

Inner Belt

50. Inner Belt
51. Elastic Belt Webbing
52. Gusset for Right End
53. Gusset for Left End
54. Velcro Connection Right Loop End
55. Velcro Connection Left Loop End
56. Velcro Connection Back Loop to Outer Belt
57.-59. Not Used

Inner Belt Padding

60. Inner Belt Padding
61. Lumbar Padded Section
62. Lumbar Padded Section Cover Sheet
63. Vertical Stability Battens
64. Batten Sheet Pocket
65. Hip Padded Section
66. Hip Padded Section Cover Sheet
67.-69. Not Used

Trapeze Header Options

70. Trapeze Header Options
71. Basic Belt Sewn Strap
71. (a) Belt Tab Gusset
72. Standard Belt Horizontal Loop Option
73. Premium Belt Metal Hangar Option
74.-79 Not Used

Trapeze Hangar Options

80. Trapeze Hangar Options
81. Basic Web Strap With Loop
82. Option Web Strap with Multiple Loops
83. Standard Web Strap with Slide Fastener
  (83.a) Slide Fastener
  (83.b) Strap for Slide Fastener
84. Option Web Strap with Conway Buckle
  (84.a) Conway Buckle
  (84.b) Belt with spaced holes for buckling
85. Option Quick Release Latch
  (85.a) Quick Release Latch tongue
  (85.b) Quick Release Latch receiver
86. Option Web Belt with Punched Holes and Buckle
  (86.a) Buckle with tongue
  (86.b) Lead belt end with spaced holes and belt loop
  86.(c) Attached belt end with notched loop for buckle tongue and bottom loop for keeper loop
87. Option Wire Rope with Adjustable Coupler and Ring Connector
  (87.a) 0Threaded Coupler with ring
  (87.b) Rotator knob for adjustment
  (87.c) Threaded Coupler with ring and wire rope
88. Option Sewn Strap with Loop for Handle.
89. Option Rectangular Keeper Loop

Trapeze Bar Options

90. Trapeze Bar Options
91. Wood Bar with Notched Strap Locators
92. Custom Handle Grip Wood Bar with Bolt-Ring Connector
93. Custom Molded Handle with Connector
94. Gymnastic type Ring Handles
95-99 Not Used

Device Options

100. Lumbar Supports
101. Batten Stabilizers
102. Gel Comfort Pads.
103. Plastic Support Molds
104. Overhead Arm Tension Pull Down
105. Inner Belt Abdomen Pad

DETAILED DESCRIPTION OF THE INVENTION

The present invention now will be described more fully with reference to the accompanying drawings in which the most likely embodiments will be illustrated. The invention can be embodied in many different forms; the invention should not be limited in the embodiments set forth herein. It will be readily apparent to one skilled in the art that various substitutions and modifications may be made to the invention, including embodiments anticipated by the applicant, all as set forth herein.

The primary embodiment of the invention can best be understood by the interaction of forces applied to the basic belt device and the resultant reaction of the body.

Detailed Description of the Basic Embodiment of the Invention

Figure 5:
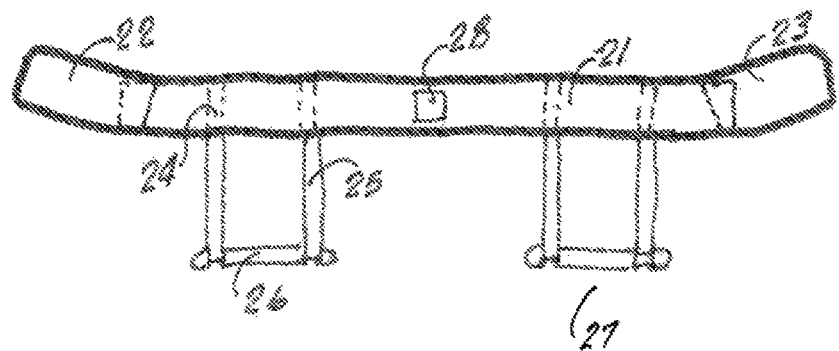

The basic device [FIG. 1, 20; FIG. 5, 20] for a wearer consists of four sections as shown: (1.) a belt section [21] around the back and sides of the girth of the waist slightly above the point of the iliac crest; (2.) a connection section [22, 23] in the front provided by fastening attachments to each end of the belt section; and (3.) a left trapeze section [27] consisting of elements [24, 25, 26]; and (4.) a right trapeze section [27] consisting of elements [24, 25, 26] centered on the left hip iliac crest and right hip iliac crest at each side of the wearer.

Downward forces by the arms pushing down against the handle of the trapeze bar [26] are transferred by gussets, loops and straps [24, 25] to the basic belt These downward compressive forces are then transferred by circumferential tension and bearing and compression forces to the body's pelvic musculature-skeletal system thus forming a foundation for resisting resultant forces. The upper body musculature-skeletal system of the shoulders is raised by the compressive forces of the arms and combined with the anchoring of the pelvic system results in the elongation of the spine thru axial tensioning.

The belt section [FIG. 1, 21] consists of a wide non elastic web strap, a heavyweight polypropylene webbing, that fits across the back and around the conical shape of the hips with the top of the belt slightly above the iliac crest, thereby inducing a downward slope toward the front connection.

The connection section consists of a Velcro fastener loop section [22] attached to the right end of the belt section and the tie section [23] attached to the left end of the belt section. The loop and tie parts are sewn to the belt sections with a slightly upward slope so the resulting Velcro connection will be horizontal across the front of the wearer.

The trapeze section [27] consists of a top gusset [24], vertical supports [25] and a handle [26]. Two web straps [25] hang from the belt section [21] and contain a loop at the lower end of each strap [FIG. 9, 72] to support the trapeze bar handle [26] where the hand grips the device. The web straps [25] are centered at the side on the iliac crest and attached to the right front and right flank of the belt and sewn at such an angle so the straps are parallel to each other when in position on the wearer.

The trapeze bar handle [26] is a cylindrical shaped part of such length to provide a comfortable grip for the hand plus attachment of the hanger straps. A section on each side of the hand grip space is reduced in diameter to form a notch for securely holding the hang strap loops as they are slid over the end of the handle to position.

Detailed Description of the Standard Embodiment of the Invention

Figure 2:
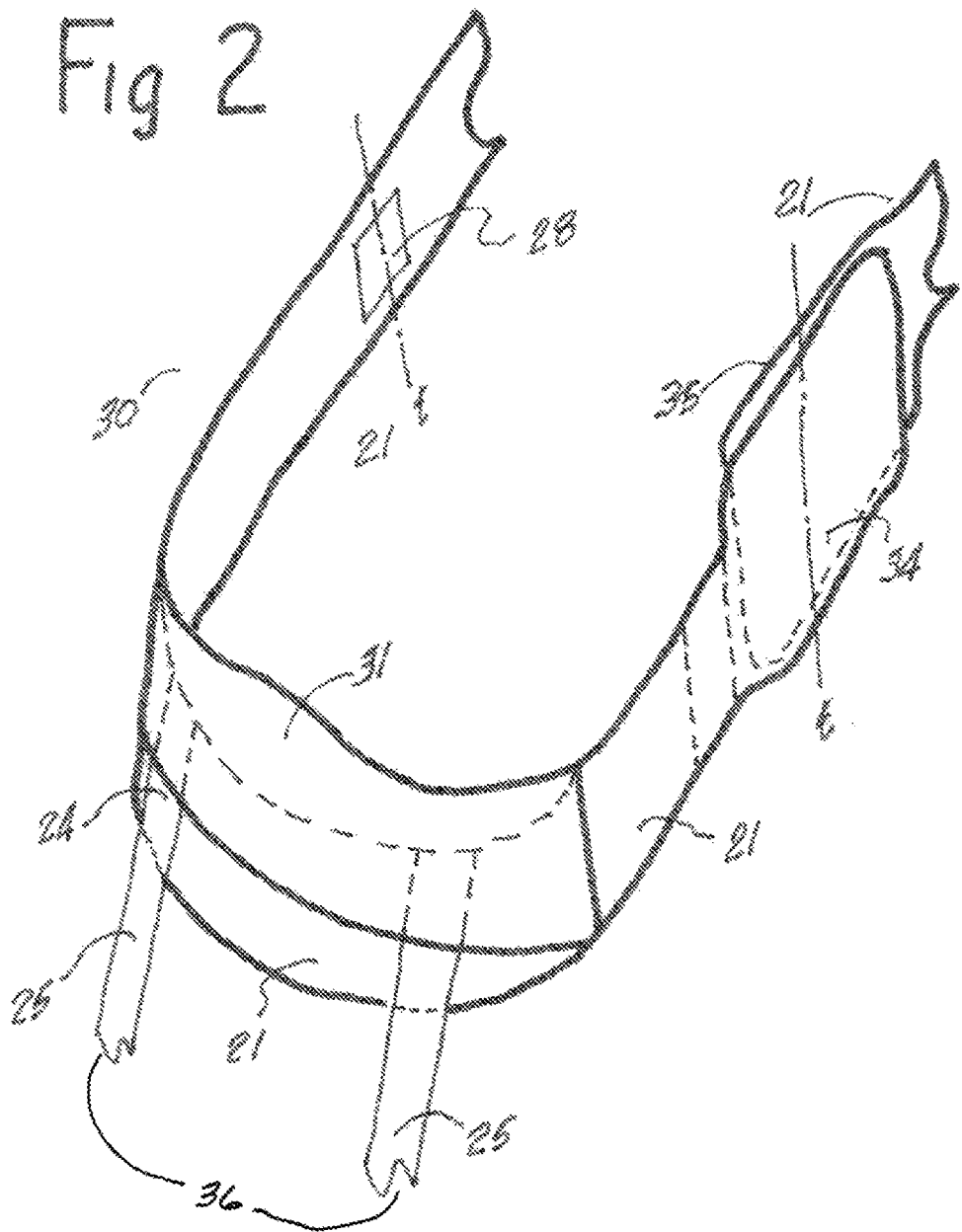
FIG. 2. Isometric View of the Top Belt Option—Standard Belt
Figure 6:
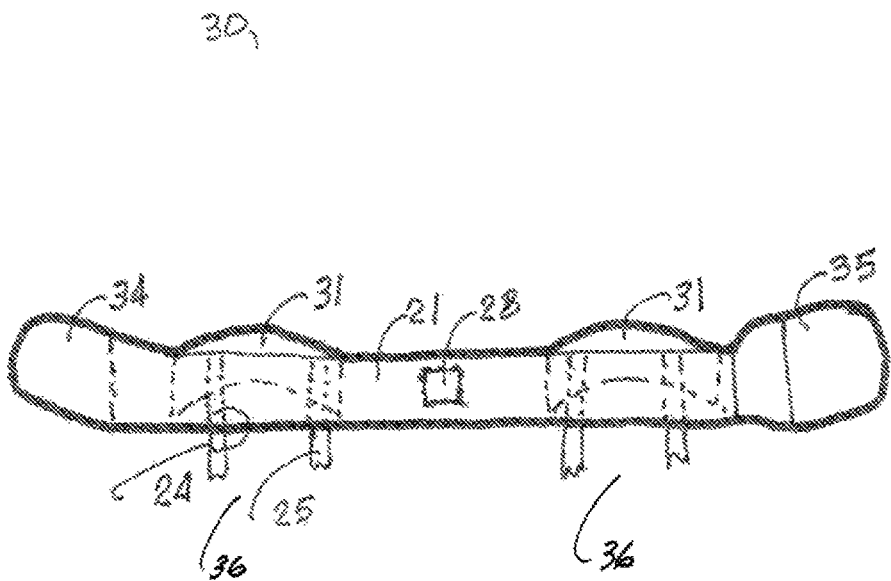
FIG. 6. Plan view—Inside of Top Belt Option—Standard Belt
FIG. 7. Plan view—Inside of Bottom Belt Option—Premium Belt.

The belt section of the standard embodiment [FIG. 2, 21; FIG. 6, 21] of the invention is improved by the addition of an overlapping belt segment [31] placed slightly above the top of the basic belt centered on the sides at the point of the iliac crest. The path of the "top belt" segment traverses the surface of a conical shape with a lesser slope than the basic belt, thus diverting forces to be supported by the iliac and the pelvic musculature-skeletal foundation system as vertical forces. The two conical belt sections are sewn along the trace line of the intersection of the greater slope of the basic belt section and the lower slope of the top belt section.

The connection section of the standard embodiment [FIG. 2, 34; FIG. 2, 35] of the invention is improved by increasing the size and shape of both the loop [34] and tie parts [35] of the Velcro connection to provide both horizontal and vertical adjustment for the variance of waist size and variance in the conical slope of the wearer's body shape. The resultant design is a loop part in the shape of a palm [34] that is smaller than a similar but larger tie part [35] to provide proper fit for horizontal and vertical variances.

The trapeze section of the standard embodiment [FIG. 2, 36; FIG. 6, 36] of the invention is improved by an alternate changing the single strap with end loop [FIG. 9, 72] to provide vertical adjustment with a hanger strap support consisting of a top gusset with tab loop [FIG. 10, 71] holding a rectangular loop ring [89] and a handle strap support consisting of a rectangular loop ring [89] supporting a bottom sewn strap with loop [FIG. 10, 88] for a handle. The standard web strap with slide fastener [83] with slide adjustment [83.a] threads thru the top and bottom rectangular loop rings [89] to adjust the height of the trapeze.

An added improvement for the standard embodiment of the invention [FIG. 2, 30; FIG. 6, 30] is an inner belt [FIG. 4, 50] which provides more comfort, support and stability for the back. This Inner Belt consists of (1) an elastic belt section [51] which is wider than the basic belt and fits across the back and around the hips of the wearer, 2: a connection section [54, 55] at the front that consists of a Velcro fastener with the loop part attached to the right end of the belt section [54] and the tie part attached to the left end of the belt section [55], and 3: padded sections for comfort and fit [61, 65] consisting of padding contained by a cover fabric [62, 66] sewn to the inside surface of the inner belt.

Figure 4:
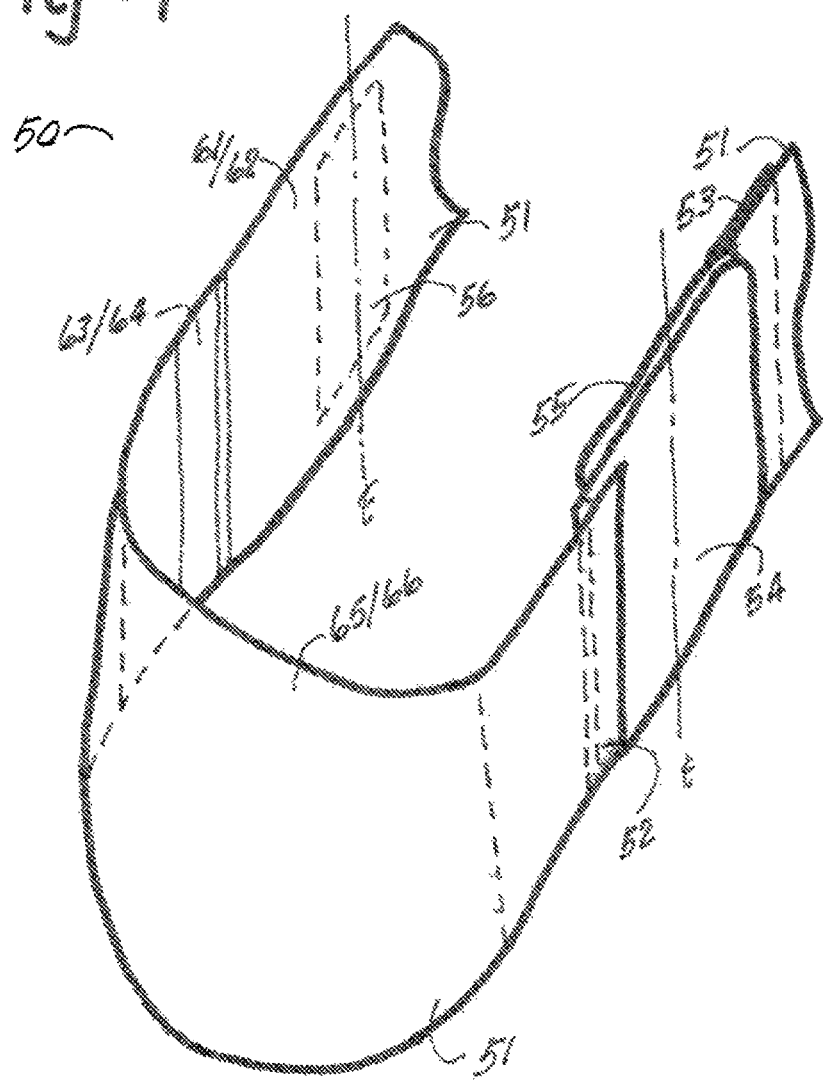
Figure 8:
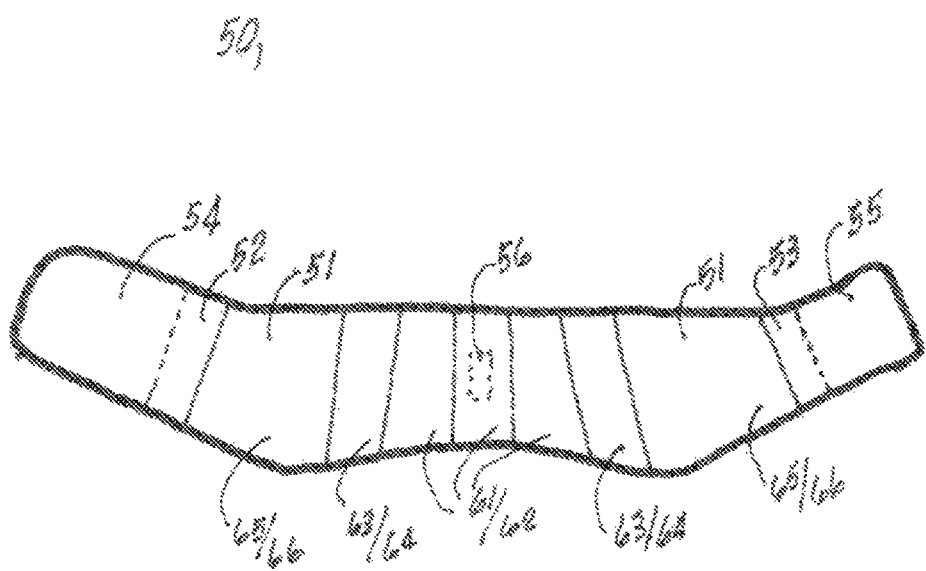
FIG. 8. Plan view—Inside of Elastic Inner Liner Belt Option—All Belts
FIG. 9. Option Web Strap with Multiple Loops.

The elastic belt section [FIG. 4, 51; FIG. 8, 51] consists of a woven elastic fabric with characteristics for elongation, breathability, workability and comfortability. The elastic belt section [51] is attached to the standard belt [FIG. 2, 21] by sewing a gusset section to the elastic back section [56] and then fastening the gusset to the standard belt [FIG. 2, 28] by sewing or by Velcro fasteners.

The padded and pocketed sections [FIG. 4; 61, 63, 65] consist of various compressible or stiffening materials to improve comfort and stability.

The padded and pocketed cover fabric sections [FIG. 4; 62, 64, 66] consist of washable woven elastic fabric and non-elastic materials appropriate for containing the inserted pads.

The connection on the inner belt to connect to the outer belt [FIG. 4; 56] consists of a Velcro Loop part on the inner belt [56] which fastens to a Velcro Tie part on the outer belt [FIG. 2, 28.]

Other Embodiments and Options

Belt Section—Premium Option Lower Belt

Figure 3:
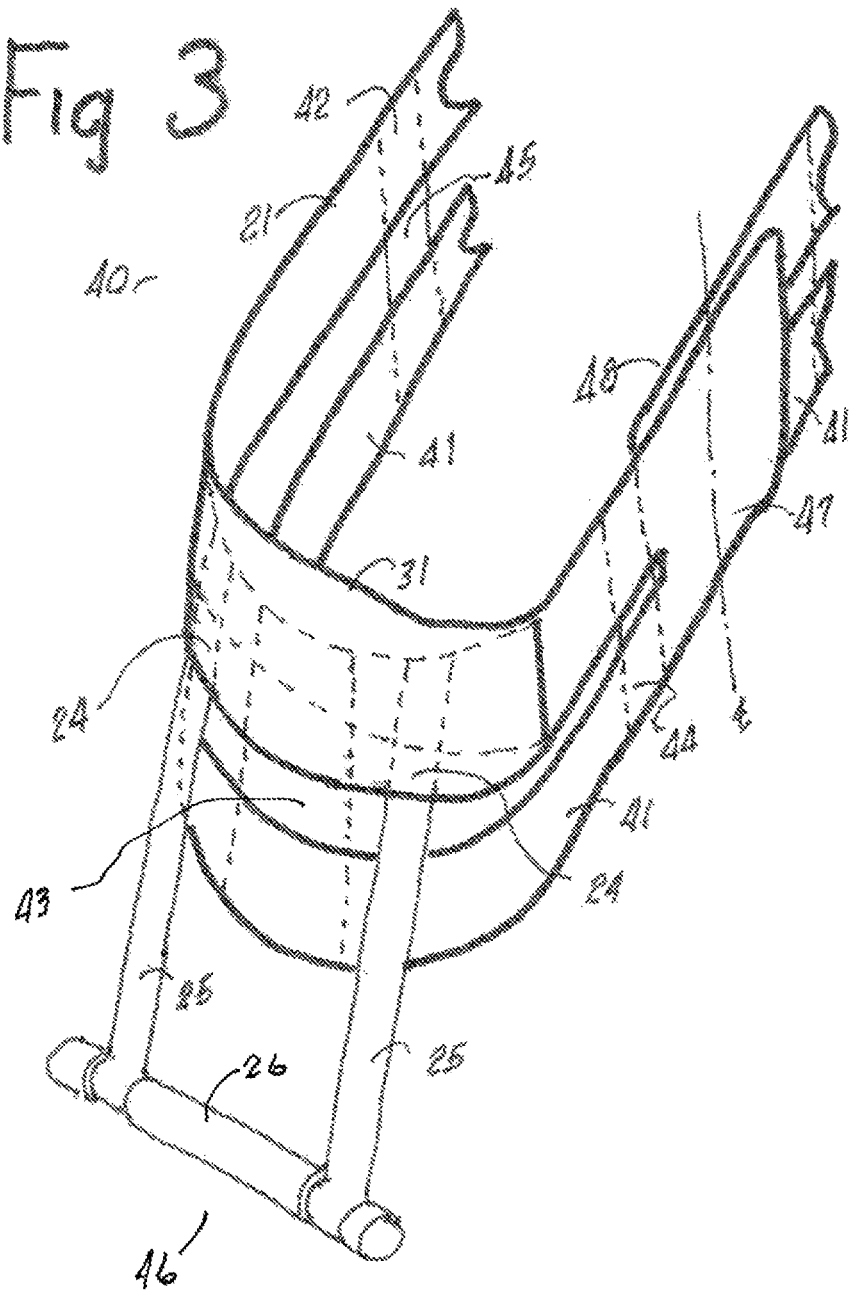
FIG. 3. Isometric View of Bottom Belt Option—Premium Belt
FIG. 4. Isometric View of Elastic Inner Liner Belt Option—All Belts
FIG. 5. Plan view—Inside of Basic Belt.
Figure 7:
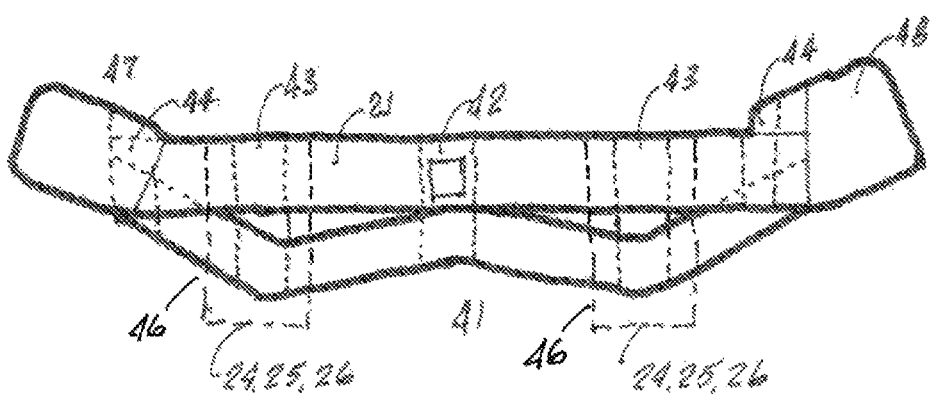

The distribution of forces to the pelvic musculature-skeletal system which provides the foundation for resultant forces in use of the standard device [FIG. 2, 30] is improved by the addition of a [FIG. 3, 41; FIG. 7, 41] lower overlapping belt. This "lower belt" consists of a gusset in the center of the back

[42] where it overlaps the lower portion of the basic belt [21] and then slopes downward to a side gusset [43] centered on the iliac crest. From the side gusset [43] a belt section [21] proceeds to slope upward to a gusset at the front [44.] The four gussets [41, 42, 43, 44] are sewn to the basic belt [21] and the front gussets [44] are sewn to the [47] loop and [48] tie ends of the Velcro connection.

The material for the lower belt [41] and gussets [42, 43, 44] consist of non-elastic woven polyethylene or other appropriate material.

Connector Section—Adjustable Connection Options

The front connector section of the device [FIG. 1: 22, 23; FIG. 2: 34, 35; FIG. 3: 47, 48] has several options for making secure connections for the left end of the belt to the right end: (1) a common Belt and Buckle Option consisting of the leader end of a belt with punched holes being attached to the back section of the right end of the belt and the buckle end of the belt attached to the front side of the left end of the belt; and, (2) a commercially available Eyelet and Cord Option consisting of eyelets being attached to gussets sewn to both ends of the back section with a cord to be threaded thru and looped around the eyelets and tied to secure the connection; and, (3) a commercially available Quick Release Cam Device consisting of the male end being attached to the right end of the belt section and the female end attached to the left end to secure engagement of the two parts; and, (4) a commercially available Blevins Buckle connection consisting of a leading edge section attached to the right end of the belt and perforated with spaced holes that slide over the studs of the male section of the device and then inserted in the female section which is attached to the left end of the belt.

Trapeze Section—Options

Figure 9:
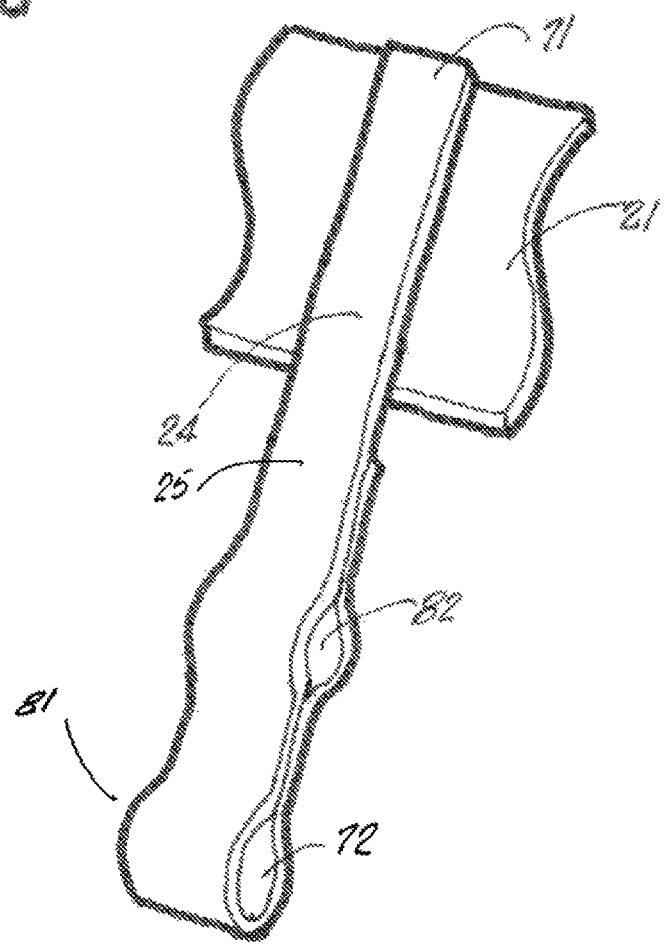
Figure 10:
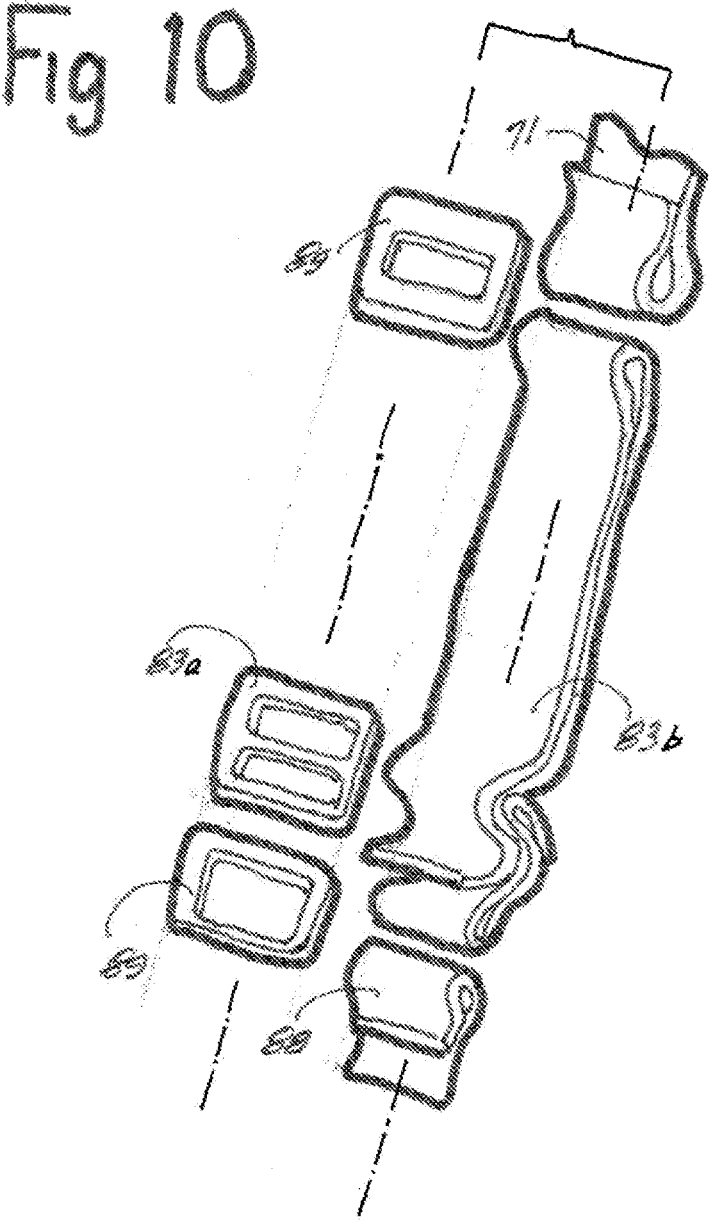
FIG. 10. Option Web Strap with Slide Fastener
FIG. 11. Option Web Strap with Conway Buckle
FIG. 12. Option Web Strap with Quick Release Fastener
FIG. 13. Option Web Strap with Punched Holes and Buckle
FIG. 14. Opposite Threaded Coupler with Ring Connectors

Options for the header portion of the trapeze support [FIG. 9, 71] consist of: (1) addition of a bottom loop to the gusset as shown in [FIG. 10, 71(a)] for connection to a rectangular loop [89]; and, (2) an alternative D ring or spring swivel trigger latch could be used; and, (3) a metal clip hangar with cutouts that function as a rectangular loop or a ring connection.

Figure 11:
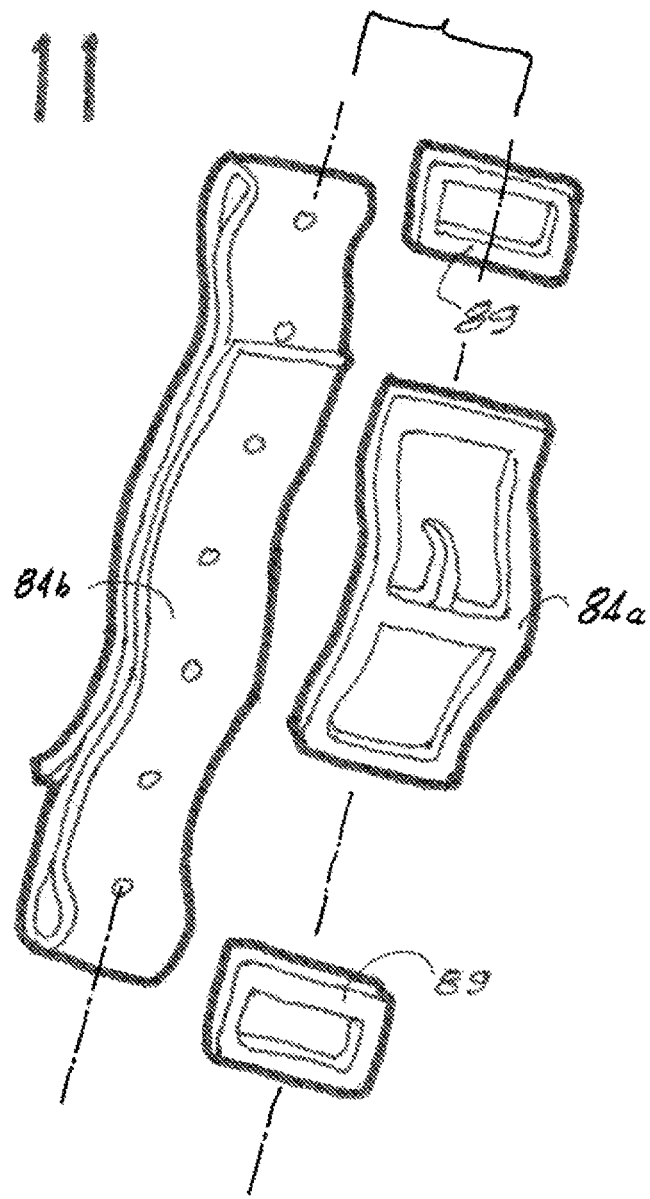
Figure 12:
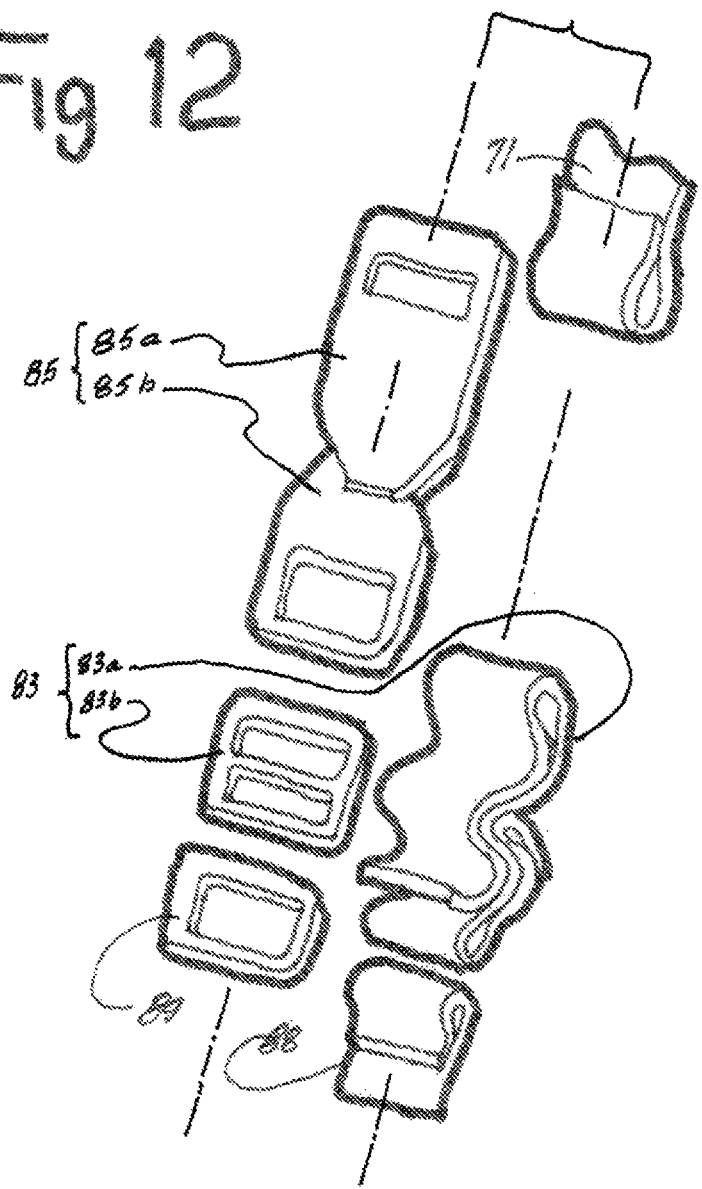
Figure 13:
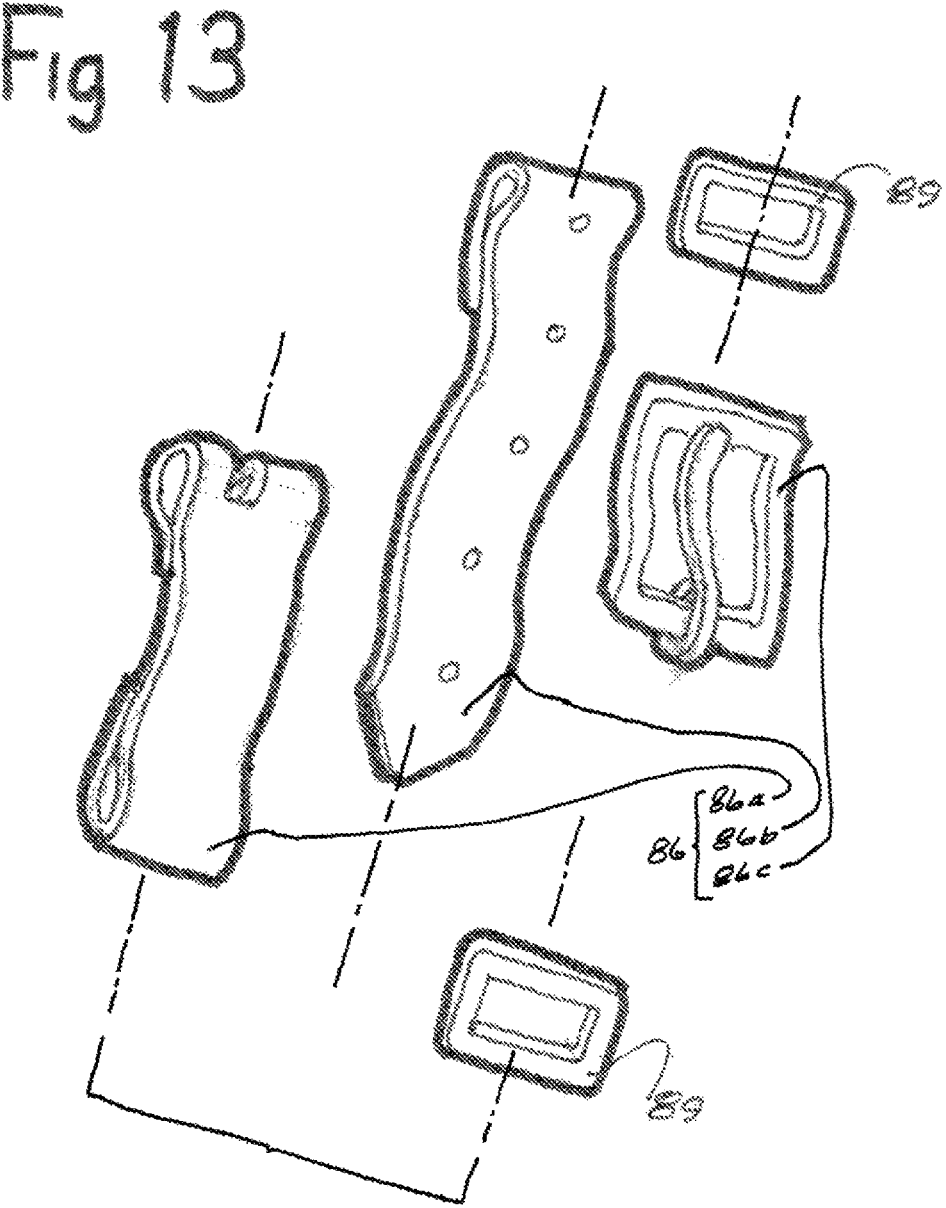
Figure 14:
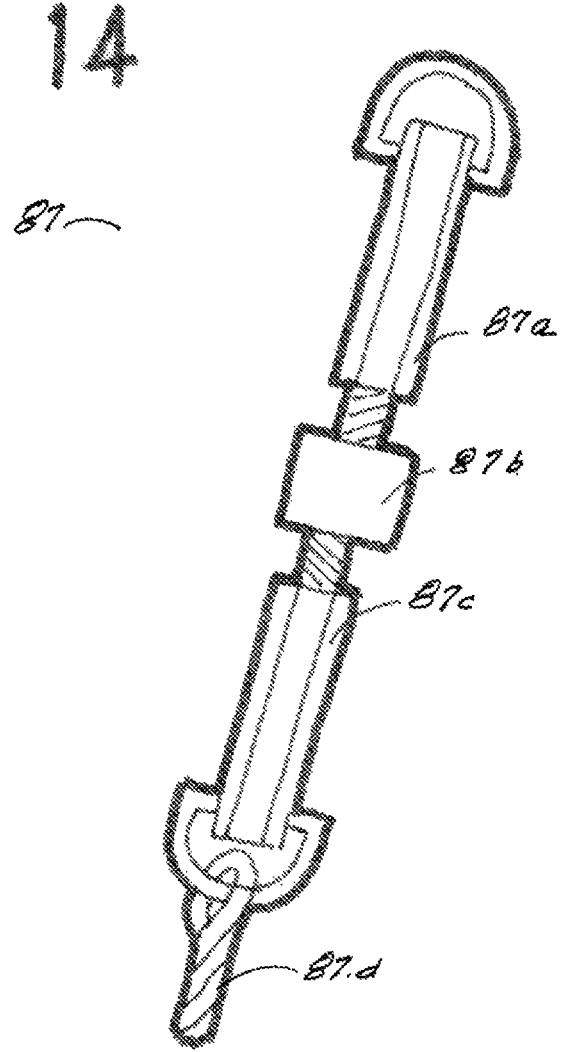

Options for the hanger portion for the trapeze support [FIG. 1, 25; FIG. 2, 25; FIG. 3, 25] consist of: (1) a Conway Buckle [FIG. 11, 84(a)] with a belt [84(b)] that has punched holes and threads through rectangular loop rings supported by the gusset at the top [89] and bottom [89]; and, (2) a belt [FIG. 13, 86] with buckle [86(c)] that makes the similar connections to the rectangular loops [89]; and, (3) an adjustable threaded coupler [FIG. 14, 87] with a rotator [87(b)] having opposite threaded bolts that screw into coupling nuts [87(a); 87(c)] with rings for attaching to web straps for connection to the belt and handle.

Options for the trapeze bar portion [FIG. 1, 26] of the trapeze assembly [FIG. 1, 26; FIG. 2, 36; FIG. 3, 26] consist of: (1) shaped handles [91] turned by lathe for more comfortable fit of the hands; and, (2) molded handles with loop ends similar to [88] or inserted coupling nuts similar to [FIG. 14, 87]; and, (3) gymnastic type ring handles. Additional adjustments are provided by various hangar options known to those skilled in the trade.

Inner Belt—Options

Options for the inner belt [FIG. 4] include: (1) special lumbar support devices [100] which are shaped to meet methods of applying pressure around the lumbar area; and, (2) formed plastic devices [102] for improved fit around the hips and improved transfer of pressure and stresses; and, (3) special plastic pads [103] capable of being filled to various pressures and attached to the inner belt by Velcro fasteners.

Further Options

An alternate embodiment of the trapeze section [90] provides for axial tensioning of the spine to occur by grasping an overhead arm tension pull down [104] which consists of a horizontal bar supported by a compressive frame on each side of the body. The user by pulling down on the horizontal bar transfers the forces downward to the trapeze web straps [FIG. 1, 25] as in the basic embodiment. Furthermore, a pad [105] may be connected at desired points inside of the belt for application of overpressure at specific points of the abdomen or lumbar region.

Use of the Invention

Use of the invention requires proper sizing, fit and fastening for the back support to attain expected performance. Three measurements are taken to determine sizing: (1) the girth of the waist from a location slightly above the iliac crest; and, (2) the girth of the pelvis taken on a slope from a point at the center of the back above the iliac crest and sloping downward in both directions around the hip to a point slightly below the navel; and, (3) a girth of the hips taken approximately three inches below the iliac crest. The invention is sized based on waist measurements in increments for girths from small to extra-extra large.

To wear the back support with proper fit, the wearer places the back support around the body, as in putting on a belt, with the two free ends in front. The elastic inner belt should be stretched so the handles are centered on each side of the body and then after inhaling, the wearer should snugly fasten the inner elastic belt with the tie and loop fasteners. At this stage, the inner belt can be slightly shifted for more comfort by tugging on the belt in the desired direction. The free ends of the non elastic outer belt should be hanging freely from the frontal ties to the inner belt and the ends should be grasped and tugged forcefully to extend the left end and place it firmly against the inner belt while fastening the loops of the right end of the outer belt by overlaying the fastening ties already in place. On some embodiments of the invention the back portion of the outer belt is secured to the side gussets and the back portion can be adjusted for the handles to remain at the sides. Other embodiments of the invention allow for adjusting the hanger length for the handles to better accommodate the arm length of the wearer.

With the back support in place as described above, the support acts as a harness around the pelvic area allowing the upper muscular skeletal framework of the shoulders to elongate and axially tension the spine when force is applied by the arms to the trapeze bar. Exercises as prescribed by the wearer's doctor or physical therapist should be followed precisely to relieve pain, stimulate blood circulation, and strengthen muscles in a progressive approach to rehabilitation of the wearer's back.

Having thus described the invention, what is claimed as new and desired to be secured by Letters Patent is as follows:

1. A method for creating orthopedic support and axial tensioning of a spine comprising:
   (a) providing a device comprising:
      a belt for wearing around a waist of a user;
      left and right trapeze sections attached to the belt,
      each trapeze section including a handle and two flexible but inelastic straps,
      each strap having an upper end attached to the belt and a lower end attached to the handle;
   (b) attaching the belt around the waist slightly above an iliac crest; and
   (c) grasping the handles with a respective hand and thrusting the arms towards the feet while lifting the shoulders upward towards the head to apply simultaneously a downward force to each trapeze to transfer the force through the belt for distribution to the pelvic region and lower body musculature and an upward force to the shoulder region for distribution of forces to the upper body musculature resulting in axial tensioning of the spine.

2. The method as claimed in claim 1, wherein the belt comprises a top belt addition having an additional belt segment attached to and overlapping a top portion of an outside perimeter of the belt, the additional belt segment extending beyond points of attachment of the straps and having a top edge with a conical shape.

3. The method as claimed in claim 1, wherein the belt is adjustable to provide changes in length of the belt and position and length of the straps.

4. The method as claimed in claim 1, wherein the thrusting of arms by a user provides self administration and control of the applied forces that can be adjusted to a level of pain.

5. The method as claimed in claim 1, wherein the axial tensioning of the spine can be accomplished without a harness compressing the chest cavity, thereby facilitating breathing, or without supports under the arms which subject the user to an increased level of blood clots.

6. The method as claimed in claim 1, wherein the axial tensioning of the spine provides sufficient traction to increase the separation between the vertebrae of the spine, reducing the compression of the spinal discs, and stimulating circulation of blood to the spinal cord and strengthening muscles of the back associated with good posture.

\* \* \* \* \*